(12) United States Patent
Iwataki et al.

(10) Patent No.: US 6,476,055 B1
(45) Date of Patent: Nov. 5, 2002

(54) 5,5-DISUBSTITUTED THIAZOLIDINE DERIVATIVE PESTICIDES

(75) Inventors: Isao Iwataki, Gainesville, FL (US); Vladimir F. Rudchenko, Moscow (RU); Thomas Kurz, Gainesville, FL (US); Charles R. Semer, IV, Gainesville, FL (US); Thomas A. Kucharek, Gainesville, FL (US); Detlef Geffken, Hamburg (DE)

(73) Assignee: Nippon Soda Co. Ltd., Tokyo (JP)

( * ) Notice: Subject to any disclaimer, the term of this patent is extended or adjusted under 35 U.S.C. 154(b) by 0 days.

(21) Appl. No.: 09/820,026

(22) Filed: Mar. 28, 2001

(51) Int. Cl.$^7$ ............... C07D 417/10; C07D 277/38; A61K 31/4436; A61K 31/426
(52) U.S. Cl. ............... 514/342; 514/369; 546/270.7; 548/184; 548/185
(58) Field of Search ............... 548/185, 184; 546/270.7; 514/369, 342

(56) References Cited

U.S. PATENT DOCUMENTS 4,957,933 A  *  9/1990  Geffken et al.

OTHER PUBLICATIONS

Brown et al., "Structure and Antimicrobial Activity of the 3–Aminorhodanines", J. Org Chem. vol. 24 (1959) p. 1056–1060.

Talukdar, P.B., "Studies on Dithiocarbamates. Part I. some Derivatives of Rhodanine", Indian J. Appl. Chem. vol. 28 (1965) p. 197–202.

Gassman et al., "Cyanohydrind—A General Synthesis," Paragon Press Ltd., p. 3773–3776.

Syun–ichi Kiyooka et al., "One–Pot Synthesis of a–Chloronitriles From Arylcarbonyl Compounds," The Chemical Society of Japan, (Mar. 28, 1984).

* cited by examiner

Primary Examiner—Robert W Ramsuer
Assistant Examiner—Rebecca Anderson
(74) Attorney, Agent, or Firm—Dennis G. LaPointe; Mason & Associates

(57) ABSTRACT

Fungicidal 5, 5-disubstituted thiazolidine derivatives are provided having the formula:

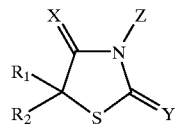

wherein R1 is C1–C6 alkyl, C1–C6 haloalkyl, C1–C6 cycloalkyl, or optionally substituted phenyl; R2 is C2–C6 alkyl or optionally substituted phenyl; X is O, NH, N—OH, substituted imino; Y is O, S, N—OH, substituted arylimino, optionally substituted alkyihydrazono, optionally substituted phenyihydrazono, or alkylsulfenyl; and Z is optionally substituted phenylamino. It is emphasized that this abstract is provided to comply with the rules requiring an abstract that will allow a searcher or other reader to quickly ascertain the subject matter of the technical disclosure.

2 Claims, No Drawings

5,5-DISUBSTITUTED THIAZOLIDINE DERIVATIVE PESTICIDES

BACKGROUND OF THE INVENTION

1. Field of the Invention

The present invention relates to novel 5,5-disubstituted thiazolidine derivatives, which have pesticidal activity. In particular, the novel 5,5-disubstituted thiazolidine derivatives of the present invention have fungicidal activity. The preparation and use, in agriculture and horticulture, of agrochemical compositions containing these novel fungicidal 5,5-disubstituted thiazolidine derivatives is also disclosed. In addition, novel methods of preparing the 5,5-disubstituted thiazolidine derivatives of the present invention are disclosed.

2. Description of the Related Art

It is known in the art that certain thiazolidine a derivatives such as those disclosed in GB-013723 have insecticidal properties. Further, it is known in the art that compounds which do not have any substituents at the 5-position of the thiazolidine ring or those that are monosubstituted or lower dialkyl substituted can be prepared using substituted hydrazines derived from a dithiocarbazate salt, $R_3NHNHC(=S)S^-M^+$, as a starting material according to Brown et al. "Structure and Antimicrobial Activity of the 3-Aminorhodanines." *J. Org. Chem. Vol.* 24. (1959), pp. 1056–1060, *J. Org .Chem. Vol.* 26. (1961), p. 5103, JP-A-1986-200978, and Talukdar, P. B. "Studies on Dithiocarbamates, Part I. Some Derivatives of Rhodamime." *Indian J. Appl. Chem. Vol.* 28. (1965), pp. 197–202. In the case of 5,5-disubstituted thiazolidine derivatives, however, when their substituent is an aryl group, cyclization to a thiazolidine ring is very difficult to achieve by known methods and side reactions occur during the cyclization reaction.

In view of the prior art at the time the present invention was made, it was not obvious to those of ordinary skill in the pertinent art how the desired 5,5-disubstituted thiazolidine derivatives having fungicidal activity could be provided.

SUMMARY OF THE INVENTION

In accordance with the present invention, 5,5-disubstituted thiazolidine derivatives are provided having the formula:

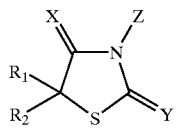

1 wherein
  $R_1$ is selected from the group consisting of $C_1$–$C_6$ alkyl, $C_1$–$C_6$ haloalkyl, $C_1$–$C_6$ cycloalkyl, and optionally substituted phenyl;
  $R_2$ is selected from the group consisting of $C_2$–$C_6$ alkyl and phenyl substituted by $A_n$;
  A is each independently selected from the group consisting of H, halogen, $C_1$–$C_6$ alkyl, $C_1$–$C_6$ haloalkyl, $C_1$–$C_6$ alkoxy, $C_1$–$C_6$ alkenyloxy, $C_1$–$C_6$ alkynyloxy, nitro, optionally substituted amino, $C_1$–$C_6$ alkylthio, $C_1$–$C_6$ alkoxycarbonyl, phenoxy, phenyl, optionally substituted pyridyl, optionally substituted thienyl, and optionally substituted furyl;
  n is 0–5;
  X is selected from the group consisting of O, NH, N—OH, optionally substituted arylimino, optionally substituted alkylimino, optionally substituted carbamoyloxyimino, optionally substituted acyloxyimino, and optionally substituted aroyloxyimino;
  Y is selected from the group consisting of 0, S, N—OH, optionally substituted arylimino, optionally substituted alkylimino, optionally substituted carbamoyloxyimino, optionally substituted sulfamoyloxyimino, optionally substituted aroyloxyimino, optionally substituted alkoxycarbonyloxyimino, optionally substituted alkylhydrazono, optionally substituted phenylhydrazono, and alkylsulfenyl; and
  Z is optionally substituted phenylamino.

The present invention also relates to the preparation of these compounds. Further, the present invention is directed to agrochemical compositions comprising as an active ingredient at least one of the novel 5,5-disubstituted thiazolidine derivatives of the present invention, as well as to the use of these active ingredients or compositions for pest control, and, in particular as fungicides useful in agriculture and horticulture.

For a better understanding of the present invention, reference is made to the following description and its scope will be pointed out in the appended claims.

DETAILED DESCRIPTION OF THE INVENTION

For purposes of the present invention the general terms used hereinabove and hereinbelow have the following meanings, unless otherwise defined:

Alkyl groups are, in accordance with the number of carbon atoms, straight-chain or branched and will typically be selected from-the group consisting of methyl, ethyl, n-propyl, isopropyl, n-butyl, sec-butyl, isobutyl, tert-butyl, n-amyl, tert-amyl, 1-hexyl, and 3-hexyl;

Cycloalkyl groups are generally selected from the group consisting of cyclopropyl, cyclobutyl, cyclopentyl, and cyclohexyl;

Halogen and halo substituents are selected from the group consisting of fluoro, chloro, bromo, and iodo, with fluoro, chloro, and bromo being the preferred substituents;

Haloalkyl may contain identical or different halogen atoms, typically selected from the group consisting of fluoromethyl, difluoromethyl, difluorochloromethyl, trifluoromethyl, chloromethyl, and trichloromethyl;

Alkoxy is typically selected from the group consisting of methoxy, ethoxy, propyloxy, isopropyloxy, n-butyloxy, isobutyloxy, sec-butyloxy, and tert-butyloxy, while methoxy and ethoxy are preferred alkoxy substituents;

Aryl is typically selected from the group consisting of substituted phenyl, substituted naphthyl, furoyl, thienyl, a six-membered heteroaromatic ring system such as pyridyl and pyrimidyl, a five-membered heteroaromatic ring such as thiazoryl, oxazoryl, pyrazoryl, thiadiazoryl and oxadiazoryl; and Aroyl is typically selected from the group consisting of substituted benzoyl, furancarbonyl, thiophenecarbonyl, and a six-membered heteroaromatic carboxylic acid residue such as nicotinyl and pyridyl.

The present invention is directed to 5,5-disubstituted thiazolidine derivatives having the following formula:

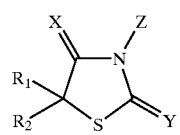

wherein
R$_1$ is selected from the group consisting of C$_1$–C$_6$ alkyl, C$_1$–C$_6$ haloalkyl, C$_1$–C$_6$ cycloalkyl, and optionally substituted phenyl;

R$_2$ is selected from the group consisting of C$_2$–C$_6$ alkyl and phenyl substituted by A$_n$;

A is each independently selected from the group consisting of H, halogen, C$_1$–C$_6$ alkyl, C$_1$–C$_6$ haloalkyl, C$_1$–C$_6$ alkoxy, C$_1$–C$_6$ alkenyloxy, C$_1$–C$_6$ alkynyloxy, nitro, optionally substituted amino, C$_1$–C$_6$ alkylthio, C$_1$–C$_6$ alkoxycarbonyl, phenoxy, phenyl, optionally substituted pyridyl, optionally substituted thienyl, and optionally substituted furyl;

n is 0–5;

X is selected from the group consisting of O, NH, N—OH, optionally substituted arylimimo, optionally substituted alkylimino, optionally substituted carbamoyloxyimino, optionally substituted acyloxyimino, and optionally substituted aroyloxyimino;

Y is selected from the group consisting of O, S, N—OH, optionally substituted arylimino, optionally substituted alkylimino, optionally substituted carbamoyloxyimino, optionally substituted sulfamoyloxyimino, optionally substituted aroyloxyimino, optionally substituted alkoxycarbonyloxyimino, optionally substituted alkylhydrazono, optionally substituted phenylhydrazono, and alkylsulfenyl; and Z is optionally substituted phenylamino.

The compounds of Formula 1, which are 5,5-disubstituted thiazolidine derivatives, one of substituents of which is an aryl, may be prepared as shown in Scheme 1 and Scheme 2 below.

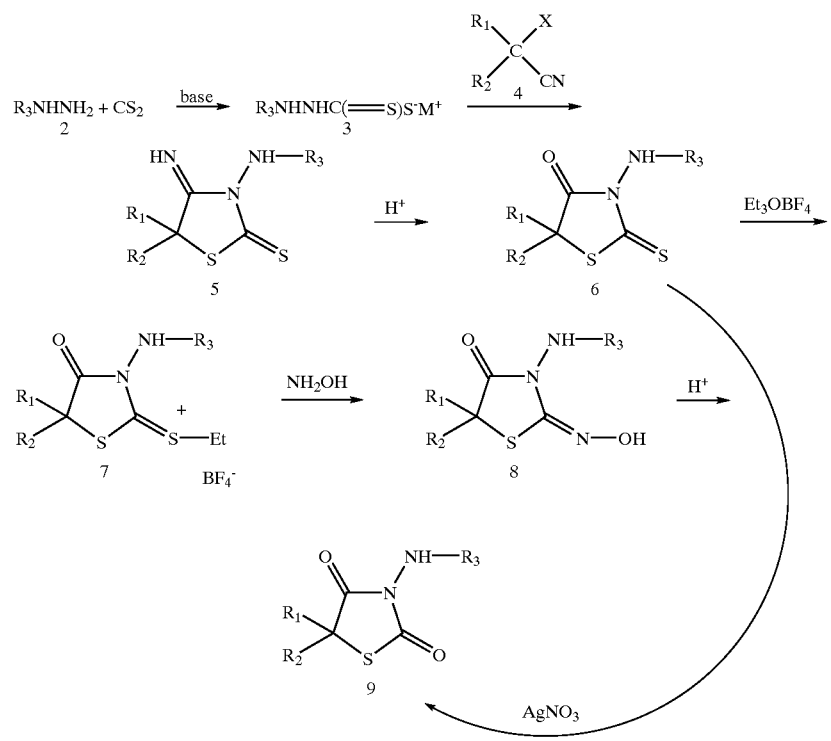

Scheme 1 wherein,
R$_1$ is selected from the group consisting of C$_1$–C$_6$ alkyl, C$_1$–C$_6$ haloalkyl, C$_1$–C$_6$ cycloalkyl, and optionally substituted phenyl;

R$_2$ is selected from the group consisting of C$_2$–C$_6$ alkyl and phenyl substituted by A$_n$;

A is each independently selected from the group consisting of H, halogen, C$_1$–C$_6$ alkyl, C$_1$–C$_6$ haloalkyl, C$_1$–C$_6$ alkoxy, C$_1$–C$_6$ alkenyloxy, C$_1$–C$_6$ alkynyloxy, nitro, optionally substituted amino, C$_1$–C$_6$ alkylthio, C$_1$–C$_6$ alkoxycarbonyl, phenoxy, phenyl, optionally substituted pyridyl, optionally substituted thienyl, and optionally substituted furyl;

M$^+$ is an ion form of a metal or tertiary amine;

n is 0–5; and

R$_3$ is optionally substituted phenyl.

As shown in Scheme 1 the chloronitriles 4, which are prepared directly by the reaction of alkyl aryl ketones with trimethylsilyl cyanide in the presence of titanium tetrachloride or by the chlorination of cyanohydrins are reacted with the dithiocarbazate salts 3 in an organic solvent such as methanol, ethanol, n-propanol, acetonitrile, ethyl acetate, acetone, methyl ethyl ketone, ether, tetrahydrofuran, benzene, chloroform, dichloromethane, N,N-dimethylformamide (DMF), dimethyl sulfoxide (DMSO) and others at 0° C. to ref lux temperature to provide the 3-substituted amino-4-imino-thiazolidine-2-thiones 5.

These resulting 3-substituted amino-4-imino-thiazolidine-2-thiones 5 are hydrolyzed with a diluted mineral acid such as hydrochloric acid or sulfuric acid at 0° C. to reflux temperature in a mixture of water and an organic solvent such as methanol, ethanol, n-propanol, acetone, tetrahydrofuran, or dioxane to provide 2-thioxo-thiazolidin-4-ones 6. The 2-thioxo-thiazolidin-4-ones 6 are transformed to the ethyl sulfenium salts 7 with triethyloxonium tetrafluoroborate in an organic solvent such as methylene chloride, chloroform, tetrahydrofuran, dioxane, diethyl ether, ethyl acetate, and others at 0° C. to reflux temperature. The replacement of the sulfenium group of the ethly sulfenium salts 7 to a hydroxyimino group 8 is carried out by the reaction of the sulfenium group with a hydroxylamine salt and a base such as sodium hydroxide, potassium hydroxide, potassium carbonate, triethylamine, pyridine and others in a solvent such as methanol, ethanol, propanol, methylene chloride, chloroform, tetrahydrofuran, dioxane, ether, DMF, DMSO and others at 0° C. to reflux temperature.

The hydrolysis of the hydroxyimino derivatives 8 to the thiazolidine-2,4-diones 9 was carried out with a mineral acid such as hydrochloric acid, sulfuric acid and others in a solvent such as methanol, ethanol, propanol, tetrahydrofuran, dioxane, DMF, DMSO and others. The thiazolidine-2,4-diones 9 may also be directly prepared by the reaction of the 2-thioxo-thiazolidin-4-diones 6 with an oxidizing reagent such as silver nitrate in a mixture of water and an organic solvent such as methanol, ethanol, propanol, dioxane, or tetrahydrofuran.

In an alternative method, the thiazolidine-2,4-diones 9 may be prepared from the reaction of thiocarbazates 11 with chloronitriles 4 in an organic solvent such as methanol, ethanol, propanol and others, followed by hydrolysis of the intermediate 4-iminothiazolidine-2-one 12 as shown in Scheme 2.

Scheme 2

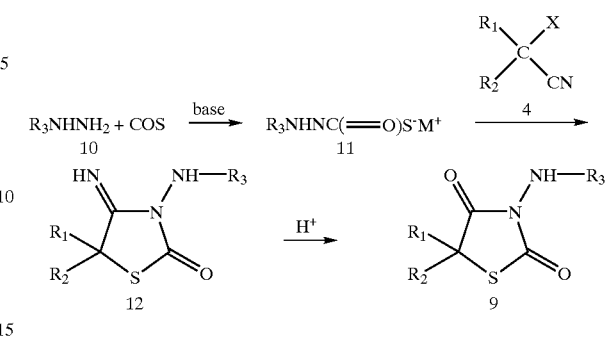

The introduction of further substituents into the 2 or 4 position of the thiazolidine ring may also conveniently be carried out by using amines and isocyanates to the corresponding imino or oximino or sulfenium derivatives as shown in Scheme 3 and Scheme 4 wherein, $R_1$ is selected from the group consisting of $C_1$–$C_6$ alkyl, $C_1$–$C_6$ haloalkyl, $C_1$–$C_6$ cycloalkyl, and optionally substituted phenyl;

$R_2$ is selected from the group consisting of $C_2$–$C_6$ alkyl and phenyl substituted by $A_n$;

A is each independently selected from the group consisting of H, halogen, $C_1$–$C_6$ alkyl, $C_1$–$C_6$ haloalkyl, $C_1$–$C_6$ alkoxy, $C_1$–$C_6$ alkenyloxy, $C_1$–$C_6$ alkynyloxy, nitro, optionally substituted amino, $C_1$–$C_6$ alkylthio, $C_1$–$C_6$ alkoxycarbonyl, phenoxy, phenyl, optionally substituted pyridyl, optionally substituted thienyl, and optionally substituted furyl;

$M^+$ is an ion form of a metal or tertiary amine;

n is 0–5;

$R_3$ is optionally substituted phenyl;

$R_4$ to $R_9$ are selected from the group consisting of lower alkyl, $C_3$–$C_6$ cycloalkyl, optionally substituted phenyl, alkylamino, and optionally substituted phenylamino; and $R_{10}$ to $R_{11}$ are lower alkyl typically selected from the group consisting of methyl, ethyl, n-propyl, isopropyl, n-butyl, sec-butyl, isobutyl, tert-butyl, n-amyl, tert-amyl, 1-hexyl, and 3-hexyl.

Scheme 3

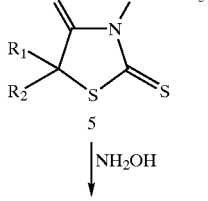 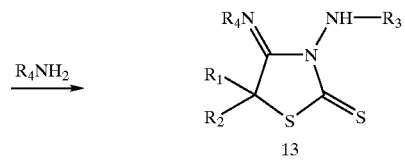

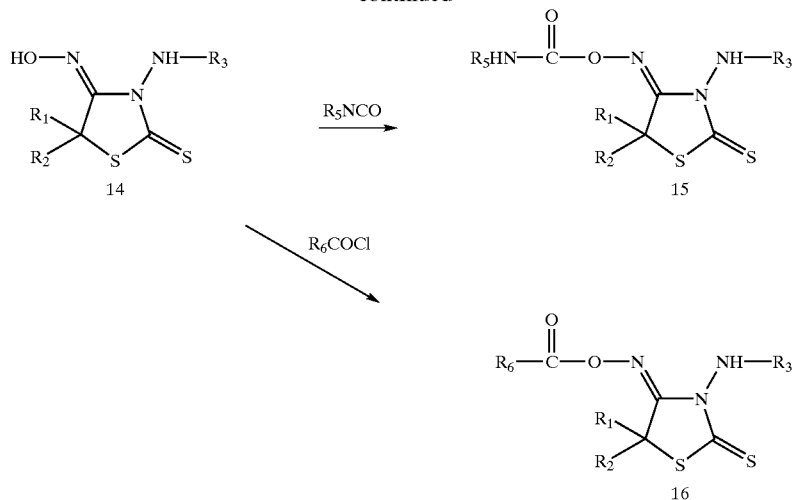

As shown in Scheme 3, the 3-substituted amino-4-imino-thiazolidine-2-thiones 5 is converted into the corresponding 4-oxyiminothiazolidines derivatives 14 with a hydroxylamine salt in an organic solvent such as methanol, ethanol, dioxane or other organic solvent. The carbamoyloxyimino derivatives 15 are prepared by the reaction of the 4-oxyiminothiazolidines 14 with substituted isocyanates in the presence of tertiary amines such as pyridine, triethylamine, and 1,8-diazabicyclo [5,4,0] undec-7-ene (DBU) in an organic solvent such as chloroform, dichloroethane, benzene, tetrahydrofuran, acetone, ethyl acetate, and DMF at 0° C. to reflux temperature.

The 4-substituted iminothiazolidine derivatives 13 are prepared by the reaction of the 3-substituted amino-4-imino-thiazolidine-2-thiones 5 with primary amines in an organic solvent such as methanol, ethanol, n-propanol, tetrahydrofuran, dioxane, DMSO, DMF, chloroform, dichloroethane and others at room temperature to reflux temperature.

The 4-acyloxyimino or 4-benzoyloxyimino or N,N-disubstituted carbamoyloxyiminothiazolidines 16 are prepared by the reaction of the 4-oxyiminothiazolidines 14 with the corresponding acyl halide or benzoyl halide or N,N-disubstituted carbamoyl chloride in the presence of tertiary amines such as triethyl amine, pyridine, DBU or an alkali metal salt such as potassium carbonate, sodium carbonate, sodium bicarbonate or a metal hydroxide in an organic solvent such as chloroform, dichloroethane, benzene, tetrahydrofuran, acetone, ethyl acetate, and DMF at 0° C. to reflux temperature.

Turning now to Scheme 4, the 2,4-diiminothiazolidine 17 are prepared by the reaction of the ethyl sulfenium salts 7 with amines in the presence of a base such as aqueous sodium hydroxide, potassium hydroxide, sodium carbonate, potassium carbonate, triethylamine, pyridine, DBU and others in water or an organic solvent such as methanol, ethanol, phentydrone (THF), dioxane, DMF, and DMSO.

Scheme 4

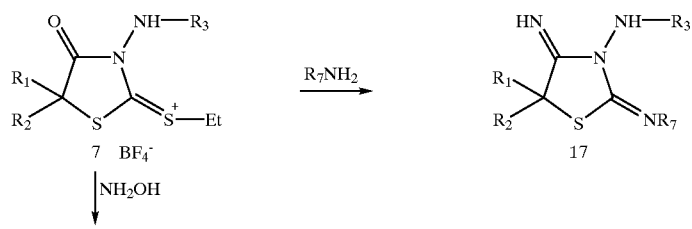

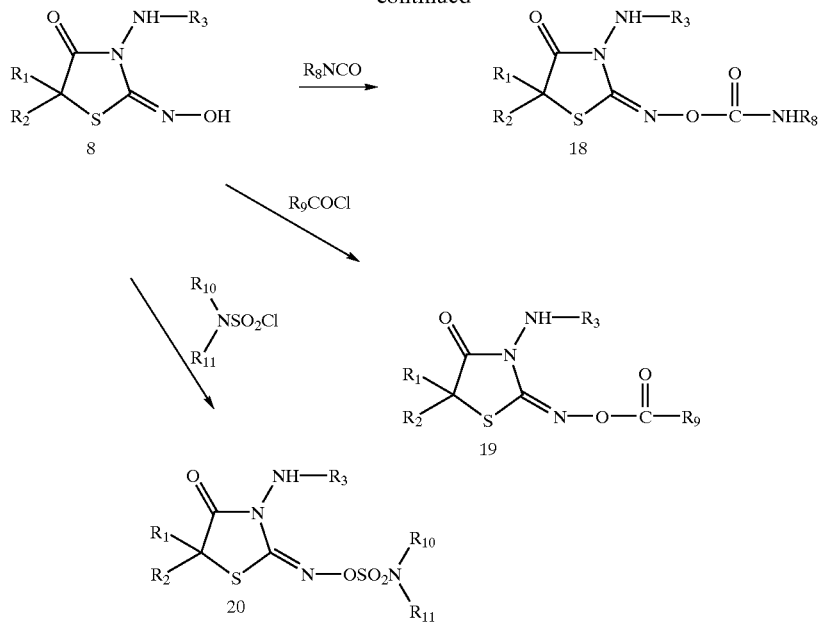

The 2-carbamoyloxyiminothiazolidines 18 are prepared by the reaction of the hydroxyimino group 8 with substituted isocyanates in the presence of tertiary amines such as pyridine, triethylamine, and DBU in an organic solvent such as chloroform, dichloroethane, benzene, tetrahydrofuran, acetone, ethyl acetate, and DMF at 0° C. to reflux temperature.

The 2-acyloxyimino or benzoyloxyimino or N,N-dialkylcarbamoyloxyiminothiazolidines 19 are prepared by the reaction of hydroxyimino group 8 with an acyl chloride or benzoyl chloride or N,N-dialkycarbamoyl chloride in the presence of tertiary amines such as pyridine, triethylamine, DBU or an alkali metal salt such as potassium carbonate or sodium carbonate in an organic solvent such as chloroform, dichloroethane, benzene, tetrahydrofuran, acetone, ethyl acetate, and DMF at 0° C. to reflux temperature.

The 2-sulfamoyloxyiminothiazolidines 20 are prepared by the reaction of hydroxyimino group 8 with an N,N-alkylsulfamoyl chloride in the presence of tertiary amines such as pyridine, triethylamine, DBU or an alkali metal salt such as potassium carbonate or sodium carbonate in an organic solvent such as chloroform, dichloroethane, benzene, tetrahydrofuran, acetone, ethyl acetate, and DMF at 0° C. to reflux temperature.

Surprisingly, it has now been found that the novel compounds of Formula 1 have, for practical purposes, a very advantageous spectrum of activities for protecting plants against diseases that are caused by fungi. The compounds of Formula 1 can be used in the agricultural field as active ingredients for controlling plants pests. These novel compounds are distinguished by their antifungal activity at low rates of application, by being well tolerated by plants and by being environmentally safe. These 5,5-disubstituted thiazolidine derivatives are useful as fungicides and are used for protecting numerous cultivated plants.

Specifically the 5,5-disubstituted thiazolidine derivatives of Formula 1 provide the control of diseases caused by a broad spectrum of plant pathogens in the ascomycete, basidomycete and oomycete classes. In addition, the 5,5-disubstituted thiazolidine derivatives of the present invention are effective in controlling a broad spectrum of plant diseases, particularly foliar pathogens of ornamental, cereal, vegetable, fruit and field crops. The 5,5-disubstituted thiazolidine derivatives of Formula 1 may be, for example, effective against the following phytopathogenic fungi: *Alternaria brassicola, Botrytis cinerea, Cercosporidium personatum, Cylindrocladium parasiticum, Didymella byroniae, Fusarium oxysporum, Fusarium solani, Peronospora tabacina, Phytophthora infestans, Phytophthora megasperma, Plasmopara viticola, Pseudopernospora cubensis, Puccinia recondita, Pythium aphanidermatum, Sclerotium rolfsii, Septoria nodorum, Venturia inaequalis* and species related to these pathogens.

The 5,5-disubstituted thiazolidine derivatives of Formula 1 are normally used in the form of compositions and can be applied to the crop and/or plant to be treated, simultaneously with or in succession with other compounds such as fertilizers, micronutrient donors or other preparations which influence the growth of plants. The 5,5-disubstituted thiazolidine derivatives of Formula 1 can also be selectively combined with herbicides, as well as, insecticides, other fungicides, bactericides, nematicides, molluscicides or mixtures of several of these preparations and, if desired together with further carriers, surfactants or application promoting adjuvants employed in the art of formulation. It has been found that the mixing of the 5,5-disubstituted thiazolidine derivatives of Formula 1 with other fungicides results, in some cases, in unexpected synergistic fungicidal activity.

EXAMPLES

The following examples serve to provide further appreciation of the invention but are not meant in any way to restrict the effective scope of the invention. The following abbreviations are used: Et=ethyl; i-propyl=isopropyl; Me=methyl; m.p.=melting point. "NMR" means Nuclear Magnetic Resonance Spectrum; "MS" means Mass Spectrum; and "%" indicates percent by weight, unless corresponding concentrations are indicated in other units. The structures of isolated novel compounds were confirmed by NMR, MS and/or other appropriate analysis.

Example 1

2-Chloro-2-(4-phenoxyphenyl)propionitrile

A mixture of 4-phenoxyphenylacetophenone (6.36 g), trimethylsilylcyanide (3.96 g) and magnesium iodide (10 mg) in methylene chloride (30 ml) was stirred for 12 hrs at room temperature, 156 hydrochloric acid (10 ml) was then added. The mixture was again stirred for 8 hrs at room temperature. The organic layer was separated and dried over anhydrous magnesium sulfate. The solvent was removed under reduced pressure. The residue was dissolved in benzene (50 ml) and pyridine (2.37 g) and thionyl chloride (4.76 g) were added at 0° C. with stirring. The reaction mixture was stirred for an additional 3 hrs at room temperature and then the solvent was evaporated. The residue was purified by column chromatography to give 7.09 g of 2-chloro-2-(4-phenoxyphenyl)propionitrile as an oil.

$^1$H-NMR(CDCl$_3$): 2.29(s, J=6.9, 3H), 6.99(d, J=6.9 Hz, 2H), 7.05(d, J=6.9 Hz, 2H), 7.24(t, J=6.8, 1H), 7.38(t, J=6.8, 2H), 7.93(d, J=6.9 Hz, 2H).

Example 2

4-Imino-5-methyl-5-phenyl-3-phenylamino-thiazolidine-2-thione 2-chloro-2-phenylpropionitrile (6.8 g) was added with stirring at 0° C. to a suspension of triethylammonium N-phenyldithiocarbazate in acetonitrile (50 ml). The mixture was then stirred for 5 hrs at room temperature. The solvent was removed under reduced pressure and the residue was purified by column chromatography (ethyl acetate-n-hexane, 1/2) to give 8.58 g of 4-imino-5-methyl-5-phenyl-3-phenylaminothiazolidine-2-thione having a melting point of 118–119° C.

Example 3

5-Methyl-5-phenyl-3-phenylamino-2-thioxo-thiazolidin-4-one

37% hydrochloric acid (5 ml) and water (1 ml) was added at room temperature with stirring to a solution of 4-imino-5-methyl-5-phenyl-3-phenylaminothiazolidine-2-thione (9.38 g) in methanol (50 ml). The solution was stirred for 24 hrs at room temperature. The solvent was then evaporated under reduced pressure. The residue was purified by column chromatography (ethyl acetate-n-hexane, 1/3) to yield an oily 5-methyl-5-phenyl-3-phenylamino-2-thioxothiazolidin-4-one (7.02 g).

$^1$H-NMR (CDCl$_3$): 2.17 (s, 3H), 6.75, 6.94, 7.39 (m, 11H).

Example 4

4-Hydroxyimino-5-methyl-5-phenyl-3-phenyl-aminothiazolidine-2-thione

A solution of 4-imino-5-methyl-5-phenyl-3-phenylaminothiazolidine-2-thione (0.31 g) and hydroxylamine hydrochloride (0.16 g) in methanol (15 ml) was refluxed for 6 hrs followed by solvent evaporation. The residue was purified by column chromatography (ethyl acetate-n-hexane, 1/3) to yield 4-hydroxyimino-5-methyl-5-phenyl-3-phenylamino-thiazolidine-2-thione (0.17 g) having a melting point of 83–84° C.

Example 5

4-(3,4-Dichlorophenylcarbamoyl)oxyimino-5-methyl-5-phenyl-3-phenylaminothiazolidine-2-thione A mixture of 4-hydroxyimino-5-methyl-5-phenyl-3-phenylamino-thiazolidine-2-thione (0.19 g), triethylamine (0.06 g) and 3,4-dichlorophenylisocyanate in tetrahydrofuran (3 ml) was stirred for 2 days at room temperature. The solvent was evaporated under reduced pressure and the residue was purified by column chromatography (chloroform) to yield 4-(3,4-Dichlorophenylcarbamoyl)oxyimino-5-methyl-5-phenyl-3-phenylaminothiazolidine-2-thione (0.13 g) having a melting point of 95–96° C.

Example 6

3-(N-Hydroxy-N-phenyl)amino-5-methyl-5-phenyl-2-thioxothiazolidine-4-one

A mixture of 5-methyl-5-phenyl-3-phenylamino-2-thioxothiazolidin-4-one (0.51 g) and m-chloroperbenzoic acid (0.3 g) in methylene chloride (10 ml) was stirred at room temperature for 3 hrs and then washed with a sodium carbonate aqueous solution. The methylene chloride solution was dried over anhydrous magnesium sulfate and the solvent was evaporated under reduced pressure. The residue was purified by column chromatography (ethyl acetate-n-hexane, 1/1) to yield 3-(N-hydroxy-N-phenyl)amino-5-methyl-5-phenyl-2-thioxo-thiazolidine-4-one (0.34 g) having a melting point of 85–86° C.

Example 7

2-Hydroxyimino-5-methyl-5-phenyl-3-phenyl-aminothiazolidine-4-one

5-Methyl-5-phenyl-3-phenylamino-2-thioxothiazolidin-4-one (0.3 g) was added to a 1M methylene chloride solution of triethyloxonium tetrafluoroborate (1 ml) at room temperature with stirring. After stirring the mixture for 24 hrs hydroxylamine hydrochloride (0.1 g) and triethylamine (0.3 g) in methanol (10 ml) were added at 0° C. The reaction mixture was again stirred for 2 hrs at room temperature followed by evaporation of the solvents under reduced pressure. The residue was added to ice water and then extracted with ethyl acetate. The ethyl acetate solution was dried over anhydrous ethyl acetate and the solvent was then evaporated under reduced pressure. The residue was purified by column chromatography (ethyl acetate-n-hexane, 1/2) to yield 2-hydroxyimino-5-methyl-5-phenyl-3-phenylaminothiazolidine-4-one (0.21 g) having a melting point of 62–63° C.

Example 8

5-(4-Bromophenyl)-3-(2,4-difluoro)phenyl-amino-5-methyl-thiazolidin-2,4-dione 5-(4-Bromophenyl)-3-(2,4-difluoro)phenylamino-5-methyl-2-thioxo-thiazolidin-4-one (0.3 g) was dissolved in 3 ml of tetrahydrofuran, silver nitrate (0.68 g) in 2 ml of water was then added with stirring at room temperature. After 3 hrs, the mixture was diluted with water and extracted with methylene chloride. The methylene chloride solution was dried over anhydrous magnesium sulfate and the solvent was evaporated. The residue was recrystallized from methanol to yield 5-(4-bromophenyl)-3-(2,4-difluoro)-phenylamino-5-methyl-thiazolidin-2,4-dione (0.23 g) having a melting point of 142–143° C.

Example 9

2-Methoxyimino-5-methyl-5-phenyl-3-phenyl-aminothiazolidin-4-one

5-Methyl-5-phenyl-3-phenylamino-2-thioxothiazolidin-4-one (0.87 g) was mixed with a 1M methylene chloride solution of triethyloxonium tetrahydroborate (3 ml) at room temperature. The reaction mixture was stirred overnight at room temperature. Methoxyamine hydrochloride (0.25 g) and triethylamine (0.61 g) in methanol (10 ml) were then added at room temperature to the mixture. After 1 hr, the solvents were evaporated under reduced pressure. The residue was purified by column chromatography (chloroform) to yield 2-methoxyimino-5-methyl-5-phenyl-3-phenylaminothiazolidin-4-one (0.38 g) having a melting point of 133–134° C.

Example 10

2-(4–Chlorophenyl)imino-5-methyl-5-phenyl-3-phenyl-aminothiazolidin-4-one

5-Methyl-5-phenyl-3-phenylamino-2-thioxothiazolidin-4-one (0.28 g) was mixed with a 1M methylene chloride solution of triethyloxonium tetrafluoroborate (1 ml) at room temperature. The reaction mixture was stirred for 24 hrs at room temperature then p-chloroaniline (0.25 g) in chloroform (10 ml) was added to the mixture at 0° C. The mixture was stirred at room temperature for 1 hr and then water was added. The separated oil was extracted with chloroform. The chloroform layer was dried over anhydrous magnesium sulfate and the solvent was evaporated under reduced pressure. The residue was purified by column chromatography (chloroform-n-hexane, 1/1) to yield 2-(4-chlorophenyl)imino-5-methyl-5-phenyl-3-phenylaminothiazolidin-4-one (0.21 g) having a melting point of 53–54° C.

The compounds of Table I can also be prepared in an analogous manner or by methods corresponding to those indicated above.

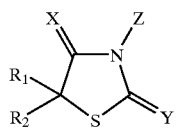

| X | Y | $R_2$ | $R_1$ | Z | Physical data m.p. °C. |
|---|---|---|---|---|---|
| O | S | phenyl | Me | phenylamino | oil, $^1$H-NMR |
| O | S | 4-chlorophenyl | Me | phenylamino | |
| NH | S | 2,4-dichloro-phenyl | Me | phenylamino | |
| NOMe | S | 4-tolyl | Me | phenylamino | |
| O | 3,4-dichloro-benzoyloxyimino | phenyl | Me | phenylamino | 74–75 |
| O | O | 3-trifluoro-methylphenyl | Me | phenylamino | |
| O | O | 2-bromophenyl | Me | phenylamino | |
| O | O | 3-iodophenyl | Me | 2,4-dichlorophenylamino | |
| NH | S | 2,4,6-trimethylphenyl | Me | 4-chlorophenylamino | |
| O | S | 4-methoxyphenyl | Me | phenylamino | |
| N,N-dimethyl-carbamoyloxy-imino | S | 2-fluorophenyl | Me | phenylamino | |
| O | S | 3-fluorophenyl | Me | 4-chlorophenylamino | |
| O | O | 4-trifluoro-phenyl | Me | 4-methyl-phenylamino | |
| O | NOH | 2,4-dimethylphenyl | Me | phenylamino | |
| O | O | phenyl | $CF_3$ | phenylamino | |
| O | S | 4-tolyl | Me | phenylamino | |
| O | O | 4-nitrophenyl | Me | 4-fluoro-phenylamino | |
| O | O | 3,4-dichlorophenyl | Me | phenylamino | |
| NH | S | 2,6-difluorophenyl | Me | phenylamino | |
| O | S | phenyl | $CF_3$ | phenylamino | 93–94 |
| NOH | S | 2,4-difluorophenyl | Me | phenylamino | |
| O | ethoxy-carbonyloxy-imino | phenyl | Me | phenylamino | |
| O | 2,4-dimethyl-benzoyl-oxyimino | 2,4-dichlorophenyl | Me | phenylamino | |
| O | O | 4-tolyl | Me | phenylamino | |
| O | S | phenyl | Me | 2,4,6-trichloro-phenylamino | |
| NH | S | 2-bromophenyl | Me | phenylamino | |
| O | O | phenyl | Me | phenylamino | oil, $^1$H-NMR |
| O | N-2,4-dichlorophen-oxycarbamoyl-oxyimino | phenyl | Me | phenylamino | |
| O | S | 2,4-dichlorophenyl | Me | phenylamino | |
| O | NOH | 3-trifluoro-methylphenyl | Me | phenylamino | |
| O | N,N-dimethyl-sulfamoyl-oxyimino | phenyl | Me | phenylamino | 219–220 |
| O | O | 4-phenoxyphenyl | Me | 4-chlorophenylamino | |
| O | S | 4-ethoxy-carbonylphenyl | Me | phenylamino | |
| O | O | phenyl | Et | phenylamino | |

-continued

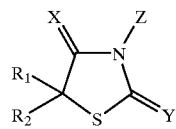

| X | Y | R₂ | R₁ | Z | Physical data m.p. ° C. |
|---|---|---|---|---|---|
| O | NOH | 4-biphenyl | Me | phenylamino | 225–226 |
| O | S | 2-chloro-4-methylphenyl | Me | phenylamino | |
| N-3,4-dichlorophenylcarbamoyl-oxyimino | S | phenyl | Me | phenylamino | 95–96 |
| NH | S | 3-chlorophenyl | Me | 4-fluorophenylamino | |
| O | O | 3-phenoxyphenyl | Me | phenylamino | |
| O | S | 2-bromo-4-chlorophenyl | Me | phenylamino | |
| O | 2,4-dichloro-benzoyl-oxyimino | 4-biphenyl | Me | phenylamino | 75–76 |
| O | S | 4-trifluoro-methylphenyl | Me | phenylamino | |
| NOMe | S | phenyl | Me | phenylamino | oil, ¹H-NMR |
| O | S | 3-iodophenyl | Me | phenylamino | |
| O | S | 3,4-dimethoxyphenyl | Me | phenylamino | |
| O | O | 4-fluorophenyl | Me | phenylamino | |
| O | NOMe | 2,6-difluorophenyl | Me | phenylamino | |
| NOH | S | 4-phenoxyphenyl | Me | phenylamino | |
| O | O | 2-tolyl | Me | phenylamino | |
| O | S | 3-fluorophenyl | Me | phenylamino | oil, ¹H-NMR |
| O | N—OH | 4-tolyl | Me | 2-fluorophenylamino | |
| O | O | 4-phenoxyphenyl | Me | phenylamino | 65–66 |
| O | S | 3-methoxyphenyl | Me | phenylamino | |
| NH | S | 4-bromophenyl | Me | 2,4-difluoro-phenylamino | 132–133 |
| O | S | 4-nitrophenyl | Me | phenylamino | |
| NH | S | 2-methyl-4-chlorophenyl | Me | phenylamino | |
| O | O | 4-{2-(5-tri-fluoromethyl-3-chloro)-pyridyloxy}phenyl | Me | phenylamino | |
| NH | S | 3,5-dichlorophenyl | Me | phenylamino | |
| O | 2,6-dichloro-phenylimino | 4-phenoxyphenyl | Me | phenylamino | 69–70 |
| O | S | 4-biphenyl | Me | phenylamino | 154–155 |
| NOH | S | 4-tolyl | Me | phenylamino | |
| O | O | phenyl | i-propyl | phenylamino | |
| NH | S | 4-biphenyl | Me | phenylamino | 183–184 |
| O | O | phenyl | phenyl | phenylamino | |
| O | 4-chlorophenyl-hydrazono | phenyl | Me | phenylamino | 74–75 |
| O | O | 2-pyridyl | Me | phenylamino | |
| O | S | 3,4-methylenedioxyphenyl | Me | phenylamino | |
| O | NOMe | phenyl | Me | phenylamino | 133–134 |
| O | S | 2,4-difluorophenyl | Me | phenylamino | |
| O | N,N-dimethyl carbamoyl-oxyimino | 4-biphenyl | Me | phenylamino | 187–188 |
| O | O | 2-thienyl | Me | phenylamino | |
| O | S | 3-bromophenyl | Me | phenylamino | |
| O | 4-chloro-phenylimino | phenyl | Me | phenylamino | 53–54 |
| O | O | phenyl | Me | phenylamino | |
| N-4-chlorophenyl-carbamoyl-oxyimino | S | phenyl | Me | phenylamino | |
| NH | S | 4-t-butylphenyl | Me | phenylamino | |
| O | N-4-methylphenyl-carbamoyl-oxyimino | phenyl | Me | 4-fluorophenylamino | |
| O | O | 2-furyl | Me | phenylamino | |
| NOH | S | phenyl | Me | phenylamino | 83–84 |
| O | O | 4-acetamidophenyl | Me | phenylamino | |
| O | S | phenyl | Me | 2,3,4,5,6-pentafluoro-phenylamino | |
| O | N-ethoxy-carbonyl-oxyimino | 4-phenoxyphenyl | Me | phenylamino | 55–56 |
| NH | S | 4-biphenyl | Me | 4-fluorophenylamino | 158–159 |
| O | O | 2,3,4-trichlorophenyl | Me | phenylamino | |

-continued

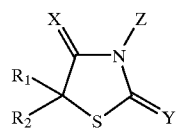

| X | Y | R₂ | R₁ | Z | Physical data m.p. ° C. |
|---|---|---|---|---|---|
| O | S | 4-propargyloxy-phenyl | Me | phenylamino | |
| O | NOH | phenyl | Me | phenylamino | 62–63 |
| O | N-t-butyl-carbamoyl-oxyimino | 4-phenoxyphenyl | Me | phenylamino | 81–82 |
| O | O | 4-isopropyl-phenyl | Me | phenylamino | |
| O | S | 4-trifluoro-methylphenyl | Me | phenylamino | |
| O | NOH | 4-bromophenyl | Me | 2,4-difluorophenylamino | 188–189 |
| O | O | 4-chlorophenyl | i-propyl | phenylamino | |
| O | S | 3-nitrophenyl | Me | phenylamino | |
| O | NOH | 4-phenoxyphenyl | Me | phenylamino | 183–184 |
| O | O | 4-biphenyl | Me | phenylamino | 96–97 |
| O | S | 3-chloro-4-methylphenyl | Me | phenylamino | |
| O | NOH | 4-biphenyl | Me | 4-fluorophenylamino | 220–221 |
| O | O | 3,5-dichlorophenyl | Me | phenylamino | |
| O | S | 2,4,6-trimethyl-phenyl | Me | phenylamino | |
| O | O | 3-chloro-4-methoxyphenyl | Me | phenylamino | |
| O | O | 3-methoxyphenyl | Me | Phenylamino | |
| NH | S | phenyl | Me | phenylamino | 118–119 |
| O | O | 3-fluorophenyl | Me | phenylamino | oil, ¹H-NMR |
| O | acethoxyimino | 4-chloro-2-methylphenyl | Me | phenylamino | |
| 2,4,6-trichloro-phenylimino | S | phenyl | Me | phenylamino | |
| N-isopropyl-carbamoyl-oxyimino | S | 2,4-dichlorophenyl | Me | phenylamino | |
| acethoxyimino | S | phenyl | Me | phenylamino | |
| O | S | 3,5-dimethyl | Me | phenylamino | |
| O | t-butylimino | 4-phenoxyphenyl | Me | phenylamino | |
| NOH | S | 4-bromophenyl | Me | phenylamino | |
| O | O | 4-bromophenyl | Me | 2,4-difluoro-phenylamino | 142–143 |
| N-methyl-carbamoyl-oxyimino | S | 3-fluorophenyl | Me | phenylamino | |
| O | chloroacethoxy | 4-tolyl | Me | phenylamino | |
| NH | S | 4-phenoxyphenyl | Me | phenylamino | oil, ¹H-NMR |
| O | 2,4-dichloro-phenylimino | phenyl | Me | phenylamino | |
| O | S | 2-chlorophenyl | Me | 2,4-dimethyl-phenylamino | |
| O | S | phenyl | Me | N-hydroxyphenylamino | 85–86 |
| O | O | phenyl | Me | H-acetyl-N-phenylamino | |
| i-propylimino | S | 4-bromophenyl | Me | phenylamino | |
| O | O | 4-biphenyl | Me | 4-fluorophenylamino | 65–66 |
| O | S | 4-phenoxyphenyl | Me | phenylamino | oil, ¹H-NMR |
| O | O | 3-nitrophenyl | Me | 4-chlorophenylamino | |
| O | S | 4-biphenyl | Me | 4-fluorophenylamino | 136–137 |
| O | N-4-tolyl-carbamoyl-oxyimino | phenyl | Me | phenylamino | |
| N,N-dimethyl-carbamoylimino | S | 4-chlorophenyl | Me | phenylamino | |
| O | methyl-hydrazono | 4-phenoxyphenyl | Me | phenylamino | |
| O | S | phenyl | cyclopropyl | phenylamino | |
| O | O | phenyl | phenyl | phenylamino | |
| NH | S | 3-nitrophenyl | Me | phenylamino | |
| O | S | 4-bromophenyl | Me | 2,4-difluoro-phenylamino | 137–138 |
| O | S | phenyl | Me | N-trifluoroacetyl-phenylamino | |
| NH | S | 2,4-difluorophenyl | Me | 4-fluoro-phenylamino | |
| O | O | 4-biphenyl | Me | 4-fluoro-phenylamino | 138–139 |
| 4-chlorobenzoyl- | S | 3-bromophenyl | Me | phenylamino | |

-continued

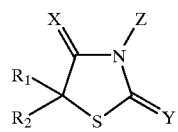

| X | Y | R₂ | R₁ | Z | Physical data m.p. ° C. |
|---|---|---|---|---|---|
| oxyimino methyl-hydrazono | S | 3-trifluoro-methylphenyl | Me | phenylamino | |
| O | S | 4-methylthiophenyl | Me | phenylamino | |

Thus while there has been described what are presently believed to the preferred embodiments of the invention, those skilled in the art will understand that other and further modifications can be made without departing from the spirit of the invention. It is intended that the present invention includes as such modifications as come within the true scope of the invention as set forth in the claims. It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A 5,5-disubstituted thiazolidine derivative having the following formula:

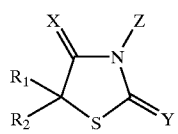

wherein $R_1$ is selected from the group consisting of $C_1$–$C_6$ alkyl, $C_1$–$C_6$ haloalkyl, $C_1$–$C_6$ cycloalkyl, and optionally substituted phenyl;

$R_2$ is phenyl substituted by $A_n$;

A is each independently selected from the group consisting of H, halogen, $C_1$–$C_6$ alky, $C_1$–$C_6$ haloalkyl, $C_1$–$C_6$ alkoxy, $C_1$–$C_6$ alkenyloxy, $C_1$–$C_6$ alkynyloxy, nitro, optionally substituted amino, $C_1$–$C_6$ alkylthio, $C_1$–$C_6$ alkoxycarbonyl, phenoxy, phenyl, optionally substituted pyridyl, optionally substituted thienyl, and optionally substituted furyl;

n is 0–5;

X is selected from the group consisting of NH, N—OH, optionally substituted arylimino, optionally substituted alkylimino, optionally substituted carbamoyloxyimino, optionally substituted acyloxyimino, and optionally substituted aroyloxyimino;

Y is S; and

Z is optionally substituted phenylamino.

2. A fungicidal composition comprising: the 5,5-disubstituted thiazolidine derivative according to claim 1 and an agriculturally acceptable carrier.

* * * * *

UNITED STATES PATENT AND TRADEMARK OFFICE
CERTIFICATE OF CORRECTION

PATENT NO. : 6,476,055 B1
DATED : November 5, 2002
INVENTOR(S) : Isao Iwataki et al.

It is certified that error appears in the above-identified patent and that said Letters Patent is hereby corrected as shown below:

Column 5,
Line 6, replace "ref lux" with -- reflux --.

Column 6,
Scheme 2, replace "$R_3NHNC(=O)S^-M^+$" with -- $R_3NHNHC(=O)S^-M^+$ --.

Signed and Sealed this

Fifteenth Day of April, 2003

JAMES E. ROGAN
*Director of the United States Patent and Trademark Office*